US012616109B2

(12) United States Patent
Boshoven et al.

(10) Patent No.: US 12,616,109 B2
(45) Date of Patent: May 5, 2026

(54) SPINACH PLANTS RESISTANT TO PERONOSPORA FARINOSA AND STEMPHYLIUM VESICARIUM

(71) Applicant: Bejo Zaden B.V., Warmenhuizen (NL)

(72) Inventors: Jordi Cornelis Boshoven, Warmenhuizen (NL); Stefanus Johannes Kaandorp, Warmenhuizen (NL); Raimon Jozef Laan, Warmenhuizen (NL); Roelof Marinus Veenstra, Warmenhuizen (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 291 days.

(21) Appl. No.: 18/037,853

(22) PCT Filed: Nov. 24, 2020

(86) PCT No.: PCT/EP2020/083246
§ 371 (c)(1),
(2) Date: May 19, 2023

(87) PCT Pub. No.: WO2022/111797
PCT Pub. Date: Jun. 2, 2022

(65) Prior Publication Data
US 2023/0404006 A1 Dec. 21, 2023

(51) Int. Cl.
| C12N 15/82 | (2006.01) |
| A01H 1/04 | (2006.01) |
| A01H 6/02 | (2018.01) |

(52) U.S. Cl.
CPC ............. A01H 6/028 (2018.05); A01H 1/045 (2021.01); C12N 15/8279 (2013.01)

(58) Field of Classification Search
None
See application file for complete search history.

(56) References Cited

U.S. PATENT DOCUMENTS

2012/0222147 A1 8/2012 Dijkstra

FOREIGN PATENT DOCUMENTS

WO 2015036469 A1 3/2015

OTHER PUBLICATIONS

Xu et al. Nature Communication (2017)8:15275.*
Mou et al., "Screening for Resistance to Leaf Spot Diseases of Spinach," Hortscience, 2008, pp. 1706-1710, vol. 43 (6).
Shi et al., "Association Analysis and Identification of SNP Markers for Stemphylium Leaf Spot (*Stemphylium botryosum* f. sp. *spinacia*) Resistance of Spinach (*Spinacia oleracea*)," American Journal of Plant Sciences, 2016, pp. 1600-1611, vol. 7(12).
Van Treuren et al. "Acquisition and regeneration of Spinacia turkestanica Iljin and S. tetrandra Steven ex M. Bieb. to improve a spinach gene bank collection," Genetic Resources and Crop Evolution, 2020, pp. 549-559, vol. 67(3).
Xu et al. "Draft genome of spinach and transcriptome diversity of 120 Spinacia accesions," Nature Communications, 2017, pp. 1-10. vol 8.

* cited by examiner

Primary Examiner — Medina A Ibrahim
(74) Attorney, Agent, or Firm — The Webb Law Firm

(57) ABSTRACT

Provided herein are spinach plants resistant to *Peronospora farinosa* and *Stemphylium vesicarium*, and spinach plants additionally resistant to Cucumber Mosaic Virus (CMV). Also provided herein are genomic fragments providing the present resistances and use thereof for identifying spinach resistant to *Peronospora farinosa* and *Stemphylium vesicarium*, and spinach plants additionally resistant to Cucumber Mosaic Virus (CMV). Provided herein are a spinach plant resistant to *Peronospora farinosa* and *Stemphylium vesicarium*: including a genomic fragment of *Spinacia tetrandra* located on chromosome 4 between positions 8255074 and 8620598 of the spinach reference genome, the genomic fragment of *Spinacia tetrandra* lacking a lethal factor and providing *Peronospora farinosa* resistance and including a genomic fragment located on chromosome 3 and between positions 1177586 and 1271037 of the spinach reference genome providing *Stemphylium vesicarium* resistance.

Figure 1:

9 Claims, 5 Drawing Sheets
Specification includes a Sequence Listing.

SPINACH PLANTS RESISTANT TO *PERONOSPORA FARINOSA* AND *STEMPHYLIUM VESICARIUM*

CROSS REFERENCE TO RELATED APPLICATION

This application is the United States national phase of International Patent Application Number PCT/EP2020/083246, filed Nov. 24, 2020, the disclosure of which is hereby incorporated by reference in its entirety.

The Sequence Listing associated with this application is filed in electronic format via EFS-Web and is hereby incorporated by reference into the specification in its entirety. The name of the text file containing the Sequence Listing is 2303536 ST25.txt. The size of the text file is 17,351 bytes, and the text file was created on May 3, 2023.

BACKGROUND OF THE INVENTION

Field of the Invention

The present invention relates to spinach plants resistant to *Peronospora farinosa* and *Stemphylium vesicarium*, and to spinach plants additionally resistant to Cucumber Mosaic Virus (CMV). The present invention also relates to genomic fragments providing the present resistances and to the use thereof for identifying spinach resistant to *Peronospora farinosa* and *Stemphylium vesicarium*, and spinach plants additionally resistant to Cucumber Mosaic Virus (CMV).

Description of Related Art

Spinach is commercially grown worldwide for its attractive and nutritious leaves. In 2018, production of spinach was close to 26 million tons worldwide. Spinach (*Spinacia oleracea*) is a member of the Amaranthaceae family, subfamily Chenopodioideae. Other well-known family members include *quinoa* and beet. The latter is a cultivated plant of major importance for agriculture with sugar beet, red beet and Swiss chard as examples.

Regarding nutritional value, while providing only a small amount of calories (only 23 for 100 grams of cooked spinach), spinach is a rich source of vitamins A, B2 (or folate), B6, C, E and K; magnesium, manganese, calcium, potassium, iron and dietary fibre.

Spinach flowering is induced by (long) day length and under optimal conditions can reach even up to 4 generations in a year with a life cycle from seed to new harvest completed within 3 months. A bottleneck can be caused by seed dormancy.

Spinach is a wind pollinator and its pollen can reach far. A line is considered male if it converts from female or mixed flowering to (all) male flowering within a week. Female lines stay so for at least three weeks without producing any pollen. Hybrids of spinach can be produced making use of plants which have a female flowering phase and plants which have a male flowering phase as pollinator. Before the female plants develop male flowers, all female flowers are fertilized by the male plant. The setting of seeds occurs rapidly within 3 days and after that the ripening of the seed takes approximately a month.

Under optimal conditions commercial elite spinach lines are grown and harvested within days to obtain baby leaf spinach.

Breeding resulted in spinach plants which are rapid growing without premature flowering. Older varieties tend to have narrower leaves and have a stronger, somewhat bitter taste; newer varieties have broader leaves and a milder taste. Also, recent types have little tendency for bolting in warm conditions and therefore will not prematurely flower and produce seeds.

Spinach is cultivated for the leaves. Commercial spinach can have round leaves of dark green color. The leaf morphology is of interest to spinach breeders. A significant share of the market of cultivated spinach is the early harvested baby leaf spinach. For spinach growers it is important that the leaves stand straight up which facilitates easy harvest, dark green colour is desired.

Spinach originates from middle Asia but it is now produced all over the world. Traditional areas where spinach was grown as a crop are Europe and Northern America, however contemporarily the biggest volume of spinach is produced in China. Spinach is produced for the food processing industry (canned or frozen spinach) as well as for the fresh market, where especially baby leaf spinach is in demand Breeders develop lines with characteristics best suited for the location or the purpose.

An important development in the production and sales of fresh spinach was the introduction of bagged spinach. For this application the desired leaf morphology is such that the leaves are not too closely packed together that are found in the partly savoyed types.

Basic types of spinach are on the market:

A savoy type with dark green, curly and crinkly leaves (for the fresh market);

A flat, or smooth, leaf spinach with broad, smooth leaves that can be cleaned easily. This type is used for industry (canned or frozen spinach, as well as processed food and baby food;

Semi savoy is an intermediate type of spinach with a comparable texture as the savoy type but easy to clean as the smooth type of spinach. It is cultivated both for fresh market and industry.

An oriental type which is heat tolerant, has long petioles, pointed leaves with several side lobes and as plant has an upright growth.

Most spinach is produced at high plant densities for fresh market production which creates the ideal environment for disease development. Additionally, there is an increasing demand to produce organic vegetables. Consumers are looking for vegetables that are obtained without the use of pesticides, fungicides, insecticides and without chemical treatment of the seed. The challenge here is that such production conditions often lead to the development of plant disease. This creates a need for spinach cultivars that encompass natural, genetically encoded resistance against pathogens.

The most common pathogens causing diseases of spinach are *Peronospora, Fusarium, Stemphyllium, Colletotrichum, Cercospora* and Cucumber Mosaic Virus. A major disease in spinach is downy mildew caused by the oomycete pathogen *Peronospora farinosa* or *Peronospora effusa* (also designated as *P. farinosa* f. sp. *spinaciae* or abbreviated Pfs). The short lifecycle of Pfs results in rapid multiplication of the pathogen on susceptible cultivars. At first, small pale yellow irregular spots appear on the upper surface of the leaves and a purple downy growth on the lower surface of the spots. Spores develop on the leaves 9-12 days after first infection and are spread by wind and splashes of water. Infected leaves are no longer attractive for consumption and prone to other, secondary (microbial) infections.

One way to combat downy mildew is to spray the plants with fungicide. This approach is highly undesirable due to its heavy impact on the environment and because it is cost and labour intense. Moreover, half of the agriculturally produced spinach is meant for the organic market and this approach is not suitable for this application. There is thus a strong need in the field for spinach with resistance against the pathogen.

*Peronospora farinosa* is a pathogen that rapidly overcomes resistance. Within 2 to 3 years newly introduced resistance genes can be broken by the pathogen and therefore there is a constant demand to identify new resistance sources. To date, seventeen official races have been described by the International Working group on *Peronospora effusa/farinosa*/Pfs (IWGP). Since only a limited set of Resistance to *Peronospora* (RPF) genes have been described that originate from *S. oleracea*, wild relatives are a potential interesting source of novel and alternative RPF genes.

A significant proportion of spinach production is grown organically therefore the demand spinach varieties having resistance to all know *Peronospora farinosa* races (presently Pfs 1-17) is high. However, in fields with fully resistant, i.e. resistant to Pfs 1 to 17, spinach cultivars the focus of growers moves from *Peronospora farinosa* to other pathogens that can affect spinach. An example of such a pathogen is the fungus *Stemphylium*, the causal agent of *Stemphylium* leaf spot. Two species of *Stemphylium* have been described to cause disease on spinach that include *Stemphylium beticola* (previously *Stemphylium botryosum*) and *Stemphylium vesicarium*. In recent years, *S. vesicarium* is the most prevalent species of the two species.

Figure 4:
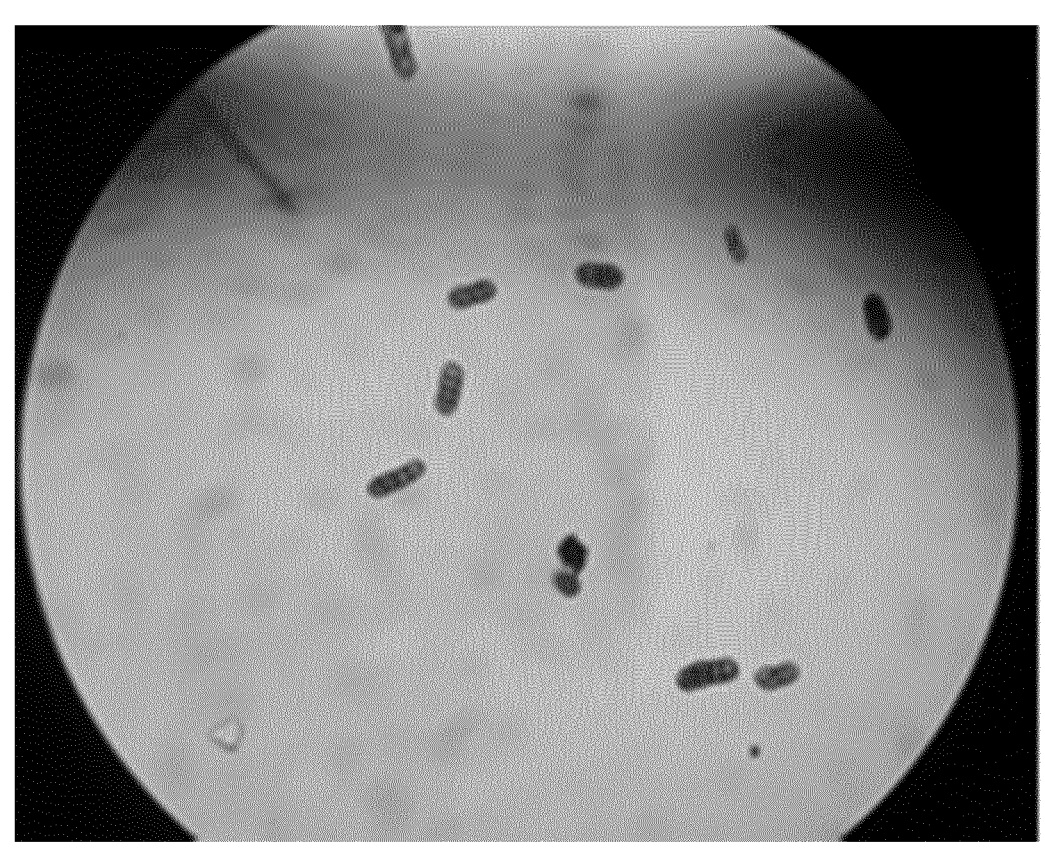
Figure 5:

*Stemphylium vesicarium* produces typical conidiospores (FIG. 4) that germinate on the leaf surface and cause small necrotic lesions on spinach leaves with brown rings (FIG. 5). Leaf spots can significantly reduce the quality and yield of spinach especially for the fresh market. Varietal differences in response to *S. vesicarium* have been observed.

Another pathogen that affects spinach production is the virus Cucumber Mosaic Virus (CMV) the causal agent of spinach blight. CMV belongs to the family of Bromoviridae and the genus *Cucumovirus*, and exhibits a broad host range of 1200 plant species in over 100 plant families Economically important crops that can suffer from CMV infection include cucurbits, pepper, lettuce, celery, tomato and beans. Genetic resistance to CMV can prevent spread of CMV especially when crop rotations with susceptible crops is normal practice. Symptoms on spinach include yellowing of the leaves, distortion of the crown leaves, rolling leaves, stunting and dying plants. Leaves with yellowing are unsuitable to sell for fresh market spinach. Therefore, genetic resistance to CMV is a welcome addition for disease resilience in spinach plants.

*Spinacia tetrandra* and *Spinacia turkestanica* are wild relatives of the contemporary spinach and both species can be sources of genetically encoded resistance to plant pathogens. Morphologically they resemble ancient spinach *Spinacia oleracea*. They are also either male or female with pointy leaves with sharp angles.

SUMMARY OF THE INVENTION

Considering the above, it is an object of the present invention, amongst other objects, to provide spinach plants, and means for obtaining these plants, exhibiting resistance for more than 1 pathogen such as two or three pathogens. The present invention especially has the object, amongst objects, to provide spinach plant resistant to *Peronospora farinosa* and *Stemphylium vesicarium*, and to spinach plants resistant to *Peronospora farinosa*, *Stemphylium vesicarium* and Cucumber Mosaic Virus (CMV).

The above objects of the present invention are met as outlined in the appended claims.

Especially, the above object, according to a first aspect, are met by providing spinach plants resistant to *Peronospora farinosa* and *Stemphylium vesicarium*, the present spinach plants comprise a genomic fragment of *Spinacia tetrandra* located on chromosome 4 of said spinach plant and between positions 8255074 and 8620598 of a spinach reference genome, said genomic fragment of *Spinacia tetrandra* lacks a lethal factor and provides *Peronospora farinosa* resistance;

the present spinach plant comprises a genomic fragment located on chromosome 3 and between positions 1177586 and 1271037 of the spinach reference genome providing *Stemphylium vesicarium* resistance.

Within the context of the present invention, "a spinach reference genome" or "the spinach reference genome" refers to the spinach genome published by Xu, C., et al., Draft genome of spinach and transcriptome diversity of 120 *Spinacia* accessions, Nature Communications 2017. Based on this publicly available spinach genome, a skilled person will readily be able to identify the corresponding positions in any spinach genome, for example by aligning the sequence of the recited genomic fragments either completely or partly.

The present inventors have surprisingly discovered that by introducing a genomic fragment of *Spinacia tetrandra* on chromosome 4 an additional resistance providing genomic fragments can be introduced on chromosome 3. However, traditionally, introducing *Peronospora farinosa* resistance on chromosome 4 was accompanied by an unwanted lethal factor effectively hampering the use of chromosome 4 for *Peronospora farinosa* resistance. The present inventors have surprisingly discovered that when a genomic fragment of *Spinacia tetrandra* located between positions 8255074 and 8620598 of the spinach reference genome was used to introduce *Peronospora farinosa* resistance, the lethal factor was absent.

According to a preferred embodiment, the present spinach plants comprise in their genomes one or more nucleotide sequences selected from the group consisting of SEQ ID Nos. 1, 3, 5, 7, 9, 11, 13, 15, 17, 19 and 21. These nucleotide sequences are correlated with *Peronospora farinosa* resistance. The nucleotide sequences comprise specific nucleotides absent in non-resistant spinach genomes, thus *Peronospora farinosa* susceptible, but present in resistant genomes. In the present description, these non-resistant variants are represented by SEQ ID Nos. 2, 4, 6, 8, 10, 12, 14, 16, 18, 20 and 22. Preferably, the present one or more are 2, 3, 4, 5, 6, 7, 8, 9, 10, or 11.

According to another preferred embodiment, the present spinach plants comprise in their genomes one or more nucleotide sequences selected from the group consisting of SEQ ID Nos. 31, 33, 35, 37, 39, 41, and 43. These nucleotide sequences are correlated with *Stemphylium vesicarium* resistance. The nucleotide sequences comprise specific nucleotides absent in non-resistant spinach genomes, thus *Stemphylium vesicarium* susceptible, but present in resistant genomes. In the present description, these non-resistant variants are represented by SEQ ID Nos. 32, 34, 36, 38, 40 and 42. Preferably, the present one or more are 2, 3, 4, 5, 6 or 7.

Considering the above, according to a more preferred embodiment, the present spinach plants comprise in their genome SEQ ID Nos. 1, 3, 5, 7, 9, 11, 13, 15, 17, 19, 21, 31, 33, 35, 37, 39, 41, and 43.

According to a more preferred embodiment, the present spinach plants further comprise a genomic fragment located on chromosome 3 and between positions 1201575 and 1220905 of the spinach reference genome providing Cucumber Mosaic Virus (CMV) resistance.

According to a preferred embodiment, the present spinach plants comprise in their genomes one or more nucleotide sequences selected from the group consisting of SEQ ID Nos. 23, 25, 27, and 29. These nucleotide sequences are correlated with Cucumber Mosaic Virus (CMV) resistance. The nucleotide sequences comprise specific nucleotides absent in non-resistant spinach genomes, thus Cucumber Mosaic Virus (CMV) susceptible, but present in resistant genomes. In the present description, these non-resistant variants are represented by SEQ ID Nos. 24, 26, 28 and 30. Preferably, the present one or more are 2, 3, or 4.

In view of the above, according to an especially preferred embodiment, the present spinach plant comprise in their genome SEQ ID Nos. 1, 3, 5, 7, 9, 11, 13, 15, 17, 19, 21, 23, 25, 27, 29, 31, 33, 35, 37, 39, 41, and 43 thereby providing spinach plants resistant to *Peronospora farinosa, Stemphylium vesicarium* and Cucumber Mosaic Virus (CMV).

Although the present genomic fragments can be introduced into spinach plants by introgression, because the nucleotide sequences of the present genomic fragments are known, these genomic fragments, for example, can be artificially constructed in yeast and subsequently allowed to recombine with susceptible spinach genomes. Alternatively, these genomic fragments can be amplified by long-range PCR amplifications and the resulting amplification fragments can be transformed into spinach cells in a single step or in a series of transformations ultimately resulting in the present spinach plants. The present genomic fragments, completely or in parts later to be reassembled, can also be isolated from gels or columns for example after restriction digestion, and subsequently transformed into spinach cells. Yet alternatively, the genomic fragments of interest can be introduced into a vector under a (strong) promotor. Subsequently, susceptible plants can be transformed with the vector and the sequence of interest would be expressed resulting in resistance.

These techniques are readily available for the skilled person. Construction of artificial chromosomes comprising the present genomic fragments is also contemplated within the context of the present invention.

Considering the above, the present invention provides a genomic source in the form of a deposit comprising all three of the present resistance providing genomic fragments. Accordingly, the present invention also relates to spinach plant wherein the present genomic fragment of *Spinacia tetrandra* providing *Peronospora farinosa* resistance, the present genomic fragment providing *Stemphylium vesicarium* resistance and the present genomic fragment providing Cucumber Mosaic Virus (CMV) resistance are obtained, originate from or are from a spinach plant deposited on 28 Oct. 2020 under deposit number NCIMB 43676 (Craibstone Estate, Ferguson Building, Bucksburn, Aberdeen AB21 9YA, United Kingdom).

According to the present invention, the *Peronospora farinosa* resistance comprises resistance to *Peronospora farinosa* isolates 1 to 17 and, preferably, additional resistance to two new *Peronospora farinosa* isolates designated UA2020-01E and SP1924.

Considering the above, the present invention, according to a second aspect, relates to combinations of a genomic fragment of *Spinacia tetrandra* located on chromosome 4 between positions 8255074 and 8620598 of a spinach reference genome, the genomic fragment of *Spinacia tetrandra* lacks a lethal factor and provides *Peronospora farinosa* resistance and a genomic fragment located on chromosome 3 and between positions 1177586 and 1271037 of the spinach reference genome providing *Stemphylium vesicarium* resistance, preferably wherein the genomic fragment of *Spinacia tetrandra* providing *Peronospora farinosa* resistance comprises one or more nucleotide sequences selected from the group consisting of SEQ ID Nos. 1, 3, 5, 7, 9, 11, 13, 15, 17, 19 and 21 and, preferably, wherein the genomic fragment providing *Stemphylium vesicarium* resistance comprises one or more nucleotide sequences selected from the group consisting of SEQ ID Nos. 31, 33, 35, 37, 39, 41, and 43.

According to a preferred embodiment, the present combinations further comprise a genomic fragment located on chromosome 3 and between positions 1201575 and 1220905 of the spinach reference genome providing Cucumber Mosaic Virus (CMV) resistance, preferably wherein the genomic fragment providing Cucumber Mosaic Virus (CMV) resistance comprises one or more nucleotide sequences selected from the group consisting of SEQ ID Nos. 23, 25, 27, and 29.

According to a third aspect, the present invention relates to the use of the present combinations as outlined the above for providing spinach plants resistant to *Peronospora farinosa* and *Stemphylium vesicarium*. The present use can comprise introgression, identification but also molecular biology techniques based on nucleic acid amplification, restriction digestion, intra- and interspecies recombination and artificial chromosome construction.

Preferably, the present combinations are additionally used for providing spinach plants resistant to *Peronospora farinosa, Stemphylium vesicarium*, and Cucumber Mosaic Virus (CMV).

According to a fourth aspect, the present inventions relates to methods for identifying a spinach plant resistant to *Peronospora farinosa* and *Stemphylium vesicarium*, the method comprises the steps of:

isolating genomic DNA from said spinach plant;

subjecting the genomic DNA to nucleic acid amplification using one or more nucleotide sequences selected from the group consisting of SEQ ID Nos. 1, 3, 5, 7, 9, 11, 13, 15, 17, 19 and 21 for establishing resistance to *Peronospora farinosa;* subjecting the genomic DNA to nucleic acid amplification using one or more nucleotide sequences selected from the group consisting of SEQ ID Nos. 31, 33, 35, 37, 39, 41, and 43 for establishing resistance to *Stemphylium vesicarium;* thereby identifying a spinach plant as resistant to *Peronospora farinosa* and *Stemphylium vesicarium*

The present method preferably further comprises the step of:

subjecting the genomic DNA to nucleic acid amplification using one or more nucleotide sequences selected from the group consisting of SEQ ID Nos. 23, 25, 27, and 29 for establishing Cucumber Mosaic Virus (CMV) resistance;

thereby further identifying said spinach plant resistant to Cucumber Mosaic Virus (CMV).

According to a sixth aspect, the present invention relates to plant cells, tissue, plant part or seed of the spinach plants detailed above.

According to a preferred embodiment of the present invention the present spinach plants detailed above are not spinach plant exclusively obtained by means of an essentially biological process.

BRIEF DESCRIPTION OF THE INVENTION

The present invention will be further detailed in the following examples. In the examples, reference is made to figures wherein:

FIG. 1: shows a representative microscopy image of *P. farinosa* f sp. *Spinaciae*.

Figure 2:
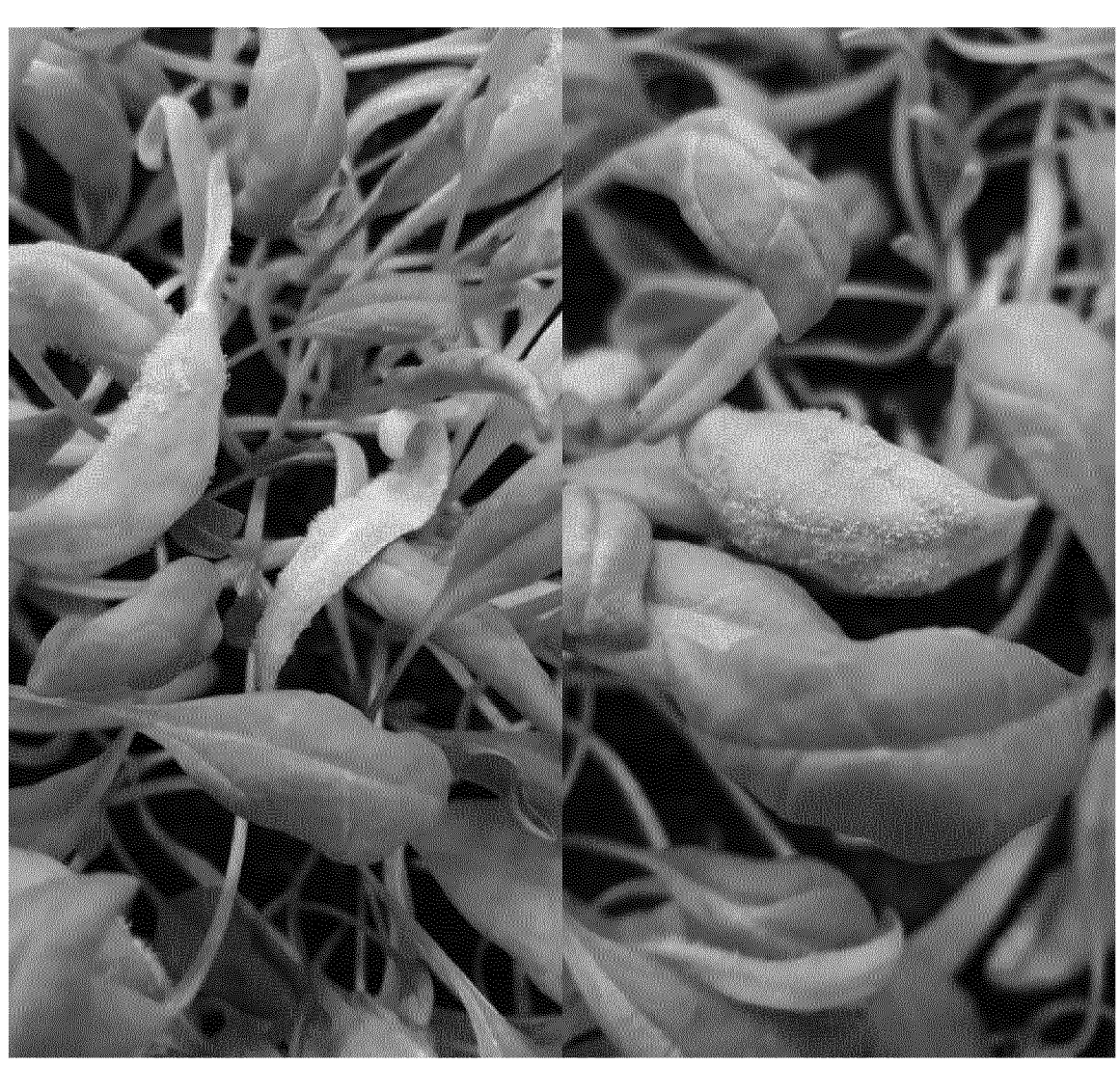

FIG. 2: shows a representative photograph of leaves of spinach plants infected with the downy mildew causative pathogen *Peronospora farinose*.

Figure 3:

FIG. 3: shows a representative photograph of a spinach plant resistant to downy mildew.

FIG. 4: shows a representative photograph of *Stemphylium* conidospores.

FIG. 5: shows a representative photograph of lesions on spinach leaves caused by *Stemphylium*.

DESCRIPTION OF THE INVENTION

Examples

Example 1. Breeding Scheme: Introducing *S. tetrandra* Genomic Fragment Comprising Pathogen Resistance into *S. oleracea*. Removal of the Lethal Factor Initially, individual plants of *S. tetrandra* were crossed with SuscA100168 (S. *Oleracea*). SuscA100168 is a female line which does not contain any downy mildew resistance. SuscA100168 has commercially desired characteristics like round and dark green leaves.
Result F1: SuscA100168 x *S. tetrandra*

Subsequently, disease assays were performed with different races of downy mildew on the hybrids. Per individual hybrid plant, resistant and vital plants were put together in a pollen-free bag together with SuscA100168. The hybrid-plants were flowering very female and therefore we waited for the pollen production of SuscA100168. In this generation we used SuscA100168 as a father, instead of a mother. The seeds were harvested in bulk from the hybrid plants.
Result BC1: SuscA100168 (2) x *S. tetrandra*

The seed harvested from the hybrid had the unfavorable property that all seeds harvested were sharp and formed in clusters. At first the seeds did not geminate at all, even when the embryos were grown in vitro. This is why we mechanically cut the clusters open, carefully got the individual seeds out, sowed these in normal potting soil and incubated the planted individual seeds in 4-6 degrees Celsius. Hereafter, the seeds were put at 20 degrees Celsius and the embryos were germinating. Hence, we performed downy mildew disease assay on the plants with race 11. The resistant plants were selected and crossed individually with SuscA100168 (S. *oleracea*).
Result BC2: SuscA100168 (3) x *S. tetrandra*

In the BC2, populations were selected for round seeds and the amount of seed available per cross. On the selected BC2 lots a disease assay with downy mildew race 11 was performed. Resistant plants were selected and genotyped selected for highest genetic resemblance with SuscA100168. Selected plants are individually crossed with SuscA100168.
Result BC3: SuscA100168(4) x *S. tetrandra*

A downy mildew disease assay with race 11 was performed on the BC3 plants. A selection was made in the resistant plants for plant that genetically resembled SuscA100168. The selected plants were selfed. In addition a second batch of seedlings was tested for resistance against race 15. Again, resistant plants genetically resembling SuscA100168 were selected for selfing.

Surprisingly, in all but one population of the BC3S1, about 25% of the plants died just after germination indicative for a lethal factor. Genetic tests showed a strong linkage between the lethality and the region of the genome that gives rise to the downy mildew resistance. This is likely because of incompatibility between the *S. oleracea* and *S. tetrandra* genome. A possible solution to overcome this lethality is reducing the size of the *S. tetrandra* introgression. Therefore, a plant with a unique crossover event that removes the linkage between the resistance and the lethal factor had to be identified.

Remarkably, one plant with a specific crossover event left of the resistance locus was surprisingly identified in the BC3 populations that showed resistance in a race 15 downy mildew disease assay (plant A7-13). As expected in a BC3 population, the resistance locus was heterozygous.
Result BC3S1: SuscA100168(4) x *S. tetrandra* c.o. S1 (=A86)

Next, 21 BC3S1 plants originating from this unique BC3 plant were tested for Pf 16 resistance. No sign of a lethal factor was observed. Overall, it can be concluded that a lethal factor was present at the beginning of chromosome 4 that is not present anymore in this lineage. Out of the 21 plant, 14 plants showed resistance. All 14 plants were selfed.
Result BC3S2: SuscA100168(4) x *S. tetrandra* c.o. S2 (=A172)

Genotyping the BC3S2 population showed vital plants that contained the resistance locus in a homozygous state. Offspring of one of these 14 plants had an additional crossover event right of the resistance locus, further reducing linkage drag. This population was A172-8 named Bejo T1 C0-2-1. In conclusion, the line Bejo T1 C0-2-1 comprises a genomic fragment of *S. tetrandra* that comprises resistance to pathogen incorporated in the genome of *S. oleracea*. In this line the lethal factor is no longer present. Representative seeds of Bejo T1 C0-2-1 were deposited on 28 Oct. 2020 under deposit number NCIMB 43676 (Craibstone Estate, Ferguson Building, Bucksburn, Aberdeen AB21 9YA, United Kingdom).

Example 2. Description of Spinach Downy Mildew—*Peronospora farinosa*—Disease Trial Resistance to *Peronospora farinosa* f sp. *spinaciae* (synonym *P. effusa* [hereafter Pfs]) is tested in a qualitative disease assay. In short, 10 to 14 days after untreated seed is sown in soil, a minimum of 8 plants is inoculated with a spore suspension of a single Pfs race or isolate. Pfs is maintained on a living susceptible host plant e.g. Viroflay or Blight or plant material with spores is stored for a maximum of 1 year at −20° C. Inoculated plants are incubated under plastic at high humidity (80-100%) and at a temperature ranging from 16° C.-20° C. After 24 hours plastic is removed, plants are assessed at 9 to 12 days after inoculation. When sporulation is observed on the cotyledons or true leaves a plant is considered susceptible and when no sporulation is observed a plant is considered resistant.

A differential set as described in Table 1 is included in each disease trial under the same environmental conditions to confirm the race. This differential set for Pfs was developed by the International Working Group on *Peronospora farinosa* (IWGP) and can be found on the website of the International Seed Federation (ISF). This differential set that consists of spinach varieties and near-isogenic lines (NILs) is used to determine the Pfs race. In this table "—" indicates resistance (no sporulation), "+" indicates susceptibility (sporulation), "(−)" indicates intermediate resistance (sparse sporulation on the tips of cotyledons), "n.t." indicates that the current strain was not tested. Seeds of this differential set and Pfs races can be obtained at Naktuinbouw (P.O. Box 40, NL-2370 AA, Roelofarendsveen, The Netherlands, naktuinbouw.com).

untreated seed is sown in soil, a minimum of 20 plants per line is transplanted in pots. Plants are inoculated between 14 and 20 days after sowing when the first true leaves are fully expanded. *S. vesicarium* is maintained in glycerol at −80° C. and multiplied on potato dextrose agar (PDA). Spores are harvested and counted to result in a spore suspension with a concentration of $1*10^4$ spores/mL Inoculated plants are incubated under plastic at high humidity (80-100%) and at a temperature ranging from 20° C.-22° C. After 24 hours plastic is removed, plants are assessed at 4 days after inoculation. When leaf spots are observed on the true leaves a plant is considered susceptible and when no leaf spots are observed a plant is considered resistant.

TABLE 1

IWGP Spinach differential set for Pfs. Where "−" is resistant, "+" is susceptible and "(−)" indicates intermediate resistance.

| Variety/NIL | Race Pfs | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| Viroflay | + | + | + | + | + | + | + | + | + | + | + | + | + | + | + | + | + |
| NIL5 | − | − | + | + | + | + | + | + | + | + | + | + | + | + | + | + | + |
| NIL3 | − | + | − | + | − | + | + | − | − | + | − | − | + | − | + | − | + |
| NIL4 | − | − | − | − | + | + | + | + | + | + | + | + | + | + | − | + | + |
| NIL6 | − | + | − | − | − | + | − | + | + | + | − | + | (−) | + | − | − | + |
| NIL1 | − | − | − | − | − | − | − | + | − | + | − | + | − | + | − | − | + |
| NIL2 | − | − | − | − | − | − | − | − | − | − | + | + | + | + | − | + | + |
| Whale | − | − | − | (−) | − | (−) | (−) | − | − | (−) | − | − | + | − | (−) | − | + |
| Pigeon | − | − | − | − | − | − | − | − | − | − | − | − | − | + | − | + | + |
| Caladonia | − | − | − | − | − | − | − | − | − | − | − | − | − | − | + | − | + |
| Meerkat | − | − | − | − | − | − | − | − | − | − | − | − | − | − | − | + | (−) |
| Hydrus | − | − | − | − | − | − | − | − | − | − | − | − | − | − | − | − | − |

TABLE 2

Resistance pattern of deposit NCIMB 43676. Where "−" is resistant and "+" is susceptible and "n.t." is not tested.

| Race Pfs | Deposit NCIMB 43676 |
|---|---|
| 1 | — |
| 2 | — |
| 3 | — |
| 4 | — |
| 5 | — |
| 6 | — |
| 7 | — |
| 8 | — |
| 9 | — |
| 10 | — |
| 11 | — |
| 12 | — |
| 13 | — |
| 14 | — |
| 15 | — |
| 16 | — |
| 17 | — |
| Isolate Pfs | |
| UA2020-01E | — |
| SP1924 | — |

Example 4. Description of Spinach—*Stemphylium*—Disease Trial

Resistance to *Stemphylium vesicarium* is tested in a qualitative disease assay. In short, 7 to 10 days after

| Variety | Score |
|---|---|
| Deposit NCIMB 43676 | R |
| Responder | S |
| Patton | S |

R: resistant; S: susceptible.

Example 5. Description of Spinach—CMV—Disease Trial

Resistance to CMV is tested in a qualitative disease assay. In short, 7 to 10 days after untreated seed is sown in soil, a minimum of 20 plants per line is transplanted in pots. Plants are inoculated between 14 and 20 days after sowing when the first true leaves are fully expanded. CMV is maintained as lyophilized spinach leafs at 4° C. CMV is first mechanically inoculated on *Nicotiana benthamiana* followed by a multiplication on a susceptible spinach variety. Spinach plants are assessed 10 days post inoculation. Plants with leaf yellowing are considered susceptible whereas plant without leaf yellowing are considered resistant.

| Variety | Score |
|---|---|
| Deposit NCIMB 43676 | R |
| Responder | S |

R: resistant; S: susceptible.

Example 6. Novel Resistance Against Downy Mildew from *Spinacia tetrandra*—Marker Development An inbred population was used to validate the hypothesis that the introgression from *S. tetrandra* provides resistance against *Peronospora*. The introgression fully segregated with the resistance in a disease test for race 17 (Table 3).

TABLE 3

Number of plants showing correlation between disease scores and the genotype of a SNP in an inbred population derived from *S. oleracea* and *S. tetrandra*.

| Disease score Pfs17 | SNP* homozygous (*S. tetrandra*) | SNP* heterozygous (*S. oleracea* and *S. tetrandra*) | SNP* homozygous (*S. oleracea*) |
|---|---|---|---|
| Resistant | 20 | 50 | 0 |
| Susceptible | 0 | 0 | 25 |

*chromosome 4 position 1,108,440 bp.

Selected plants with a crossover close to the resistance locus were used to further confirm the genetic location of the resistance. The region co-segregating with the resistance from *S. tetrandra* is located on chromosome 4 between 8.3 and 8.6 Mbp and can be identified with several nucleotide sequences (Table 4). Abbreviations are according to IUPAC Nucleotide code:

| Symbol | Nucleotide Base |
|---|---|
| A | Adenine |
| C | Cytosine |
| G | Guanine |
| T | Thymine |

-continued

| Symbol | Nucleotide Base |
|---|---|
| N | A or C or G or T |
| M | A or C |
| R | A or G |
| W | A or T |
| S | C or G |
| Y | C or T |
| K | G or T |
| V | Not T |
| H | Not G |
| D | Not C |
| B | Not A |

TABLE 4

SNPs for the detection of the resistance against *Peronospora farinosa*.

| SNP | Chromosome | Position Chromosome* (bp) | Scaffold | Position Scaffold (bp) | Allele linked to resistance | Alternative allele |
|---|---|---|---|---|---|---|
| 1 | chr4 | 8255074 | 37 | 851003 | G | A |
| 2 | chr4 | 8293796 | 37 | 889725 | C | T |
| 3 | chr4 | 8456792 | 37 | 1052721 | C | T |
| 4 | chr4 | 8486432 | 37 | 1082361 | T | A |
| 5 | chr4 | 8508790 | 37 | 1104719 | T | A |
| 6 | chr4 | 8508969 | 37 | 1104898 | A | G |
| 7 | chr4 | 8509446 | 37 | 1105375 | T | G |
| 8 | chr4 | 8512290 | 37 | 1108219 | T | C |
| 9 | chr4 | 8512511 | 37 | 1108440 | G | A |
| 10 | chr4 | 8605622 | 37 | 1201551 | T | A |
| 11 | chr4 | 8620598 | 37 | 1216527 | G | T |

*The reference genome is : Xu, C., et al., Draft genome of spinach and transcriptome diversity of 120 Spinacia accessions, Nature Communications 2017.

| SEQ ID No. | Genetic position* on Chr 4 (bp) | Sequence- SNP nucleotide is highlighted bold and in brackets |
|---|---|---|
| SEQ ID No. 1 | 8255074 | TCTGGGGTTTTCTGTAAATTGAAAAATTGCAGGAGGTTCCTAAAGCATTGCTCCCAGTTG GGAATCGGCCATTAGTGTCGTATGTATTGGACCTTTTGGA[G]CAAAGCAATCTCAAGGA TATTATTGTGGTTCGTTTCTTtgcttttgattgttttttaWttgGGGAAAATGGCGAAATT GKGTTGCAATATACTTGTATTTG |
| SEQ ID No. 2 | 8255074 | TCTGGGGTTTTCTGTAAATTGAAAAATTGCAGGAGGTTCCTAAAGCATTGCTCCCAGTTG GGAATCGGCCATTAGTGTCGTATGTATTGGACCTTTTGGA[A]CAAAGCAATCTCAAGGA TATTATTGTGGTTCGTTTCTTtgcttttgattgttttttaWttgGGGAAAATGGCGAAATT GKGTTGCAATATACTTGTATTTG |
| SEQ ID No. 3 | 8293796 | GACCTTTTCAACTTTAAGAAGAGATTGGACCTTATCAGCTTTAAGAATCTGTTATTGTGA CTTGAATCTAGCGAAGAAGAGGAAAGACTGAAATTCARGC[C]AAGTGAAGTGCCCCAGA AGGACACGTAATAAGATCCTAGGTGGGATGACAAAGGTGCAAAGTCCCTCGTCTATCATA AGGCACCCTGGGCTGGCTATAAT |
| SEQ ID No. 4 | 8293796 | GACCTTTTCAACTTTAAGAAGAGATTGGACCTTATCAGCTTTAAGAATCTGTTATTGTGA CTTGAATCTAGCGAAGAAGAGGAAAGACTGAAATTCARGC[T]AAGTGAAGTGCCCCAGA AGGACACGTAATAAGATCCTAGGTGGGATGACAAAGGTGCAAAGTCCCTCGTCTATCATA AGGCACCCTGGGCTGGCTATAAT |
| SEQ ID No. 5 | 8456792 | TCATTCTGATCATAATCATCTGAGAATAAACATTTCACCAAATACATGagacaattcaat caaatactGCCATATTATGCTTATTAGTTATTAGCCCGCA[C]ATCCTTTAAAGGCAATA TATACTACACCTTTCACAAATGAATGAGCCACAAACAATAATTTCTCAATCAAGCAATAA GTTAATTTACACATGCWATAACT |
| SEQ ID No. 6 | 8456792 | TCATTCTGATCATAATCATCTGAGAATAAACATTTCACCAAATACATGagacaattcaat caaatactGCCATATTATGCTTATTAGTTATTAGCCCGCA[T]ATCCTTTAAAGGCAATA TATACTACACCTTTCACAAATGAATGAGCCACAAACAATAATTTCTCAATCAAGCAATAA GTTAATTTACACATGCWATAACT |

-continued

| SEQ ID No. | Genetic position* on Chr 4 (bp) | Sequence-<br>SNP nucleotide is highlighted bold and in brackets |
|---|---|---|
| SEQ ID No. 7 | 8486432 | ATMAATCCATCTGCTCATTTATCGATTTCAGATAAACATCTTTYACCAGGTTCGtgattc<br>ttctctttctctctcttcgattTTTCTTCAGAATTAGTTa[T]Yttttctttaattattt<br>ggtCGCGATTGGTATTTTATGCCCTAATTACGTGATTGAATTGCGTTTTGAGCKTCAATT<br>TKGGATGTATTGTTTGTAGAAAG |
| SEQ ID No. 8 | 8486432 | ATMAATCCATCTGCTCATTTATCGATTTCAGATAAACATCTTTYACCAGGTTCGtgattc<br>ttctctttctctctcttcgattTTTCTTCAGAATTAGTTa[A]Yttttctttaattattt<br>ggtCGCGATTGGTATTTTATGCCCTAATTACGTGATTGAATTGCGTTTTGAGCKTCAATT<br>TKGGATGTATTGTTTGTAGAAAG |
| SEQ ID No. 9 | 8508790 | GAGTTTGATTCTTCCAGTTTCGGACASAGAGGAAAATTTCTCAAATTATCACAAAATGTA<br>ATTAACAGATGAGAAAGGTGATGGAACGAATAYGAATGTG[T]TTGAAACCCTGCTACTT<br>CTCGTGTCTCACCCATATCTGATTCTRATTTCCACCATCCTTCCAACTTTGGCATACTCC<br>AAAGCTCAAGCTTTTCAAGGGAT |
| SEQ ID No. 10 | 8508790 | GAGTTTGATTCTTCCAGTTTCGGACASAGAGGAAAATTTCTCAAATTATCACAAAATGTA<br>ATTAACAGATGAGAAAGGTGATGGAACGAATAYGAATGTG[A]TTGAAACCCTGCTACTT<br>CTCGTGTCTCACCCATATCTGATTCTRATTTCCACCATCCTTCCAACTTTGGCATACTCC<br>AAAGCTCAAGCTTTTCAAGGGAT |
| SEQ ID No. 11 | 8508969 | AAGCTCAAGCTTTTCAAGGGATGGAAAGAAAACCAAGTCAACATCTGCTCCTCCATGATT<br>TGACCCTCCTGATGTTGATGCAACCCCTTCTGCGCTGATA[A]TACTATTCTCCATAYAC<br>ACCACTTCAYTCAAATATCGTAATGTAAGGAATTTCAAATGACGCAGTTGACTCATCAAT<br>GGAAGATGCTCCAACCTTGTACA |
| SEQ ID No. 12 | 8508969 | AAGCTCAAGCTTTTCAAGGGATGGAAAGAAAACCAAGTCAACATCTGCTCCTCCATGATT<br>TGACCCTCCTGATGTTGATGCAACCCCTTCTGCGCTGATA[G]TACTATTCTCCATAYAC<br>ACCACTTCAYTCAAATATCGTAATGTAAGGAATTTCAAATGACGCAGTTGACTCATCAAT<br>GGAAGATGCTCCAACCTTGTACA |
| SEQ ID No. 13 | 8509446 | TTTTTTKACATAAATTACCATATAGTGGCTATGATTGCTGAAATTTTTCAAATCTCCCAG<br>CTCACCAACACCGTTTGACCCCCGATTCCAGCTATTTCTT[T]TTCTGCTCACTACAAAC<br>CCTGTCAGTYTATGCAGAGATGTCATGCTATTCATCCCCCGRGGCATATGYGACAAACTC<br>TTACAGCCTTGTATATCTAGGTG |
| SEQ ID No. 14 | 8509446 | TTTTTTKACATAAATTACCATATAGTGGCTATGATTGCTGAAATTTTTCAAATCTCCCAG<br>CTCACCAACACCGTTTGACCCCCGATTCCAGCTATTTCTT[G]TTCTGCTCACTACAAAC<br>CCTGTCAGTYTATGCAGAGATGTCATGCTATTCATCCCCCGRGGCATATGYGACAAACTC<br>TTACAGCCTTGTATATCTAGGTG |
| SEQ ID No. 15 | 8512290 | CCTTTCAAGTAATACAGAGTTAGGTCCAAGTTTAGGATCAGGTCAAGCAAAACAACTGTA<br>TAACCATACTCAACACAGCCCCACCGGAGTCAAGTCGAAA[T]AACCAAGTCTTTGAAAG<br>AGAAGACATGACCTTATGTTCGGRCCCAACGCACAAAATCAATAGAGTAGAAATGTACAA<br>TTCATTTCCATTGCTATGtaKtg |
| SEQ ID No. 16 | 8512290 | CCTTTCAAGTAATACAGAGTTAGGTCCAAGTTTAGGATCAGGTCAAGCAAAACAACTGTA<br>TAACCATACTCAACACAGCCCCACCGGAGTCAAGTCGAAA[C]AACCAAGTCTTTGAAAG<br>AGAAGACATGACCTTATGTTCGGRCCCAACGCACAAAATCAATAGAGTAGAAATGTACAA<br>TTCATTTCCATTGCTATGtaKtg |
| SEQ ID No. 17 | 8512511 | ATAGGTTGTTTAGAACTTTATCAATTACTactaactactccgtactctTCACTGataagt<br>tgtcaattactaacTAATTACTACATAGGTTTTGTTAAAA[G]TTGTCAATTATTAGCTA<br>TTTTTCTAACAAWGGAGGTCAATTACTAATTCGTTGTCAATTAATACGTTTTCCGCCCAA<br>TTAGTCGACTAATCACATCATAA |
| SEQ ID No. 18 | 8512511 | ATAGGTTGTTTAGAACTTTATCAATTACTactaactactccgtactctTCACTGataagt<br>tgtcaattactaacTAATTACTACATAGGTTTTGTTAAAA[A]TTGTCAATTATTAGCTA<br>TTTTTCTAACAAWGGAGGTCAATTACTAATTCGTTGTCAATTAATACGTTTTCCGCCCAA<br>TTAGTCGACTAATCACATCATAA |
| SEQ ID No. 19 | 8605622 | AGATATTTTAACCGATAATTCGATATTATCCAGCTTgtactaataataaataataaatta<br>tataatcaaatacaaaaaatatttacaattttaaaatcaa[T]tttcagTGTTATATTGT<br>TATCCAAASCCAATAAGGATAAGTTAATTATCTTATAAACGTGCAATTAATACATACAAT<br>CCTTGTAAATTCAGTTTTACTTC |
| SEQ ID No. 20 | 8605622 | AGATATTTTAACCGATAATTCGATATTATCCAGCTTgtactaataataaataataaatta<br>tataatcaaatacaaaaaatatttacaattttaaaatcaa[A]tttcagTGTTATATTGT<br>TATCCAAASCCAATAAGGATAAGTTAATTATCTTATAAACGTGCAATTAATACATACAAT<br>CCTTGTAAATTCAGTTTTACTTC |
| SEQ ID No. 21 | 8620598 | tttctttacttatatatttctcttttttcacCCTTTTACTTCTCACTACCCACATAATAA<br>CAMTCTCCCACAGTCCCACCCTTTCCCCCTCCATAWCCCA[G]CAAAATTACAAGTTCAT<br>TTCTCGTCTTTCGGGTGAGATTCTCACTGCAAAGTGACCACATTACTCTTCCaaccacaa<br>aattaattaatcaaattactaCA |

-continued

| SEQ ID No. | Genetic position* on Chr 4 (bp) | Sequence- SNP nucleotide is highlighted bold and in brackets |
|---|---|---|
| SEQ ID No. 22 | 8620598 | tttctttacttatatatttctctttttttcacCCTTTTACTTCTCACTACCCACATAATAA CAMTCTCCCACAGTCCCACCCTTTCCCCCTCCATAWCCCA[T]CAAAATTACAAGTTCAT TTCTCGTCTTTCGGGTGAGATTCTCACTGCAAAGTGACCACATTACTCTTCCaaccacaa aattaattaatcaaattactaCA |

*The reference genome is Xu, C., et al., Draft genome of spinach and transcriptome diversity of 120 Spinacia accessions, Nature Communications 2017.
Odd sequences = linked to resistance, Even sequences = alternative allele.

Example 7. Markers for Detection of CMV Resistance

We have used the following markers to identify plants that are resistant to CMV.

TABLE 5

SNPs for the detection of the resistance against CMV.

| SNP | Chromo- some | Position Chromo- some* (bp) | Scaffold | Position Scaffold (bp) | Allele linked to resistance | Alternative allele |
|---|---|---|---|---|---|---|
| 12 | Chr3 | 1201575 | 31 | 1201575 | T | A |
| 13 | Chr3 | 1216490 | 31 | 1216490 | A | T |

TABLE 5-continued

SNPs for the detection of the resistance against CMV.

| SNP | Chromo- some | Position Chromo- some* (bp) | Scaffold | Position Scaffold (bp) | Allele linked to resistance | Alternative allele |
|---|---|---|---|---|---|---|
| 14 | Chr3 | 1219873 | 31 | 1219873 | A | C |
| 15 | Chr3 | 1220905 | 31 | 1220905 | G | A |

*The reference genome is : Xu, C., et al., Draft genome of spinach and transcriptome diversity of 120 Spinacia accessions, Nature Communications 2017.

| SEQ ID No. | Genetic position* on Chr 3 (bp) | Sequence- SNP nucleotide is highlighted bold and in brackets |
|---|---|---|
| SEQ ID No. 23 | 1201575 | ccctccgtatttttttctTAATGTTATAATTGCACTATTTGAtgtttcacgtttgtcaatg cgaAACTTTAGCACAATTRGTTAGTAAGACATCACATGTC[T]GATRTCTTTATCCATTT GAATGGGCCATATGTTGGCCATATACATTTCTAAAAAGGTATGGGCTACAACGCCTACAA GTAACAACTATCATAATTATAAG |
| SEQ ID No. 24 | 1201575 | ccctccgtatttttttctTAATGTTATAATTGCACTATTTGAtgtttcacgtttgtcaatg cgaAACTTTAGCACAATTRGTTAGTAAGACATCACATGTC[A]GATRTCTTTATCCATTT GAATGGGCCATATGTTGGCCATATACATTTCTAAAAAGGTATGGGCTACAACGCCTACAA GTAACAACTATCATAATTATAAG |
| SEQ ID No. 25 | 1216490 | ATGGRAAATGTAAGTTARTTGGGGATGCACataaggtgtttgMtgaaatgtctATKAgaa atgttgtttcttggacttAGAATGATATACACTGTCGTCC[A]TTGGTTTCCAATCTTAC AtttggtttKtgttttcttaGTTTGTTTCTTTAATCAACACCARcccattttttttaaac tacCTGCAACTAYTAAWTTTCAT |
| SEQ ID No. 26 | 1216490 | ATGGRAAATGTAAGTTARTTGGGGATGCACataaggtgtttgMtgaaatgtctATKAgaa atgttgtttcttggacttAGAATGATATACACTGTCGTCC[T]TTGGTTTCCAATCTTAC AtttggtttKtgttttcttaGTTTGTTTCITTAATCAACACCARcccattttttttaaac tacCTGCAACTAYTAAWTTTCAT |
| SEQ ID No. 27 | 1219873 | CAAACTTGGAAAATAATGACAGAAAAATGCTAAGTTAATATAGGAAACTACATCATTTTC ACTCGAAAAGATTAGAGGAATTCATWTTCGTCTTCCTCCC[A]TTGAYTTCATGTGCCGT AAATCTTYTGACTGTCTATATTGGTACAAGTRATTTCAGGTATATACATTGGTTAATCCA TTTTAATCTGTATCTGCCGGTGT |
| SEQ ID No. 28 | 1219873 | CAAACTTGGAAAATAATGACAGAAAAATGCTAAGTTAATATAGGAAACTACATCATTTTC ACTCGAAAAGATTAGAGGAATTCATWTTCGTCTTCCTCCC[C]TTGAYTTCATGTGCCGT AAATCTTYTGACTGTCTATATTGGTACAAGTRATTTCAGGTATATACATTGGTTAATCCA TTTTAATCTGTATCTGCCGGTGT |
| SEQ ID No. 29 | 1220905 | TATTATGAMGGGTCAACAATTATGTAATATATAGGGAAGTAGAAAGTCTGGGATGTTACC TGAAGAGTCTCCTTGCCTGCAAAGTTTTAAGCTGCAAGAA[G]GTATTTGRCAATAATTA ATRACATTKCACAACAAAGATTATGcacattttttctttaaaaatcaaGAGAAACTTGTAG ATGTACCGTAAATAGGAACATCT |

-continued

| SEQ ID No. | Genetic position* on Chr 3 (bp) | Sequence- SNP nucleotide is highlighted bold and in brackets |
|---|---|---|
| SEQ ID No. 30 | 1220905 | TATTATGAMGGGTCAACAATTATGTAATATATAGGGAAGTAGAAAGTCTGGGATGTTACC TGAAGAGTCTCCTTGCCTGCAAAGTTTTAAGCTGCAAGAA[A]GTATTTGRCAATAATTA ATRACATTKCACAACAAAGATTATGcacatttttctttaaaaatcaaGAGAAACTTGTAG ATGTACCGTAAATAGGAACATCT |

*The reference genome is Xu, C., et al., Draft genome of spinach and transcriptome diversity of 120 Spinacia accessions, Nature Communications 2017.
Odd sequences = linked to resistance, Even sequences = alternative allele.

Example 8. Markers Used to Evaluate *Stemphylium* Resistance

In an F1S1 population derived from a *Stemphylium* susceptible and resistant *S. oleracea* line, 15 Single Nucleotide Polymorphisms (SNPs) informative between both parents were used to genotype the population. The 15 SNPs were all located on chromosome 3. A strong correlation was found between the disease score and one of the SNPs on chromosome 3 (Table 6).

TABLE 6

Number of plants showing correlation between disease scores and the genotype of a SNP in a F1S1 population derived from a *Stemphylium* susceptible and resistant *S. oleracea* line.

| Diseas score Stemphylium | SNP* homozygous (Resistant parent) | SNP* heterozygous | SNP* homozygous (Susceptible parent) |
|---|---|---|---|
| Resistant | 107 | 0 | 1 |
| Susceptible | 0 | 179 | 107 |

*chromosome 3 position 1,216,584 bp.

The region co-segregating with *Stemphylium* resistance is located on chromosome 3 between 1.1 and 1.3 Mbp and can be identified with several nucleotide sequences (Table 7). Abbreviations are according to IUPAC Nucleotide code.

TABLE 7

SNPs for the detection of the resistance against *Stemphylium*.

| SNP | Chromo- some | Position Chromo- some* (bp) | Scaffold | Position Scaffold (bp) | Allele linked to resistance | Alternative allele |
|---|---|---|---|---|---|---|
| 16 | Chr3 | 1177586 | 31 | 1177586 | C | A |
| 17 | Chr3 | 1206382 | 31 | 1206382 | T | A |
| 18 | Chr3 | 1216394 | 31 | 1216394 | G | A |
| 19 | Chr3 | 1227120 | 31 | 1227120 | A | C |
| 20 | Chr3 | 1231945 | 31 | 1231945 | T | C |
| 21 | Chr3 | 1253108 | 31 | 1253108 | A | G |
| 22 | Chr3 | 1271037 | 31 | 1271037 | G | T |

*The reference genome is : Xu, C., et al., Draft genome of spinach and transcriptome diversity of 120 Spinacia accessions, Nature Communications 2017.

| SEQ ID No. | Genetic position* on Chr 4 (bp) | Sequence- SNP nucleotide is highlighted bold and in brackets |
|---|---|---|
| SEQ ID No. 31 | 1177586 | gGCAAACGTGTMCAGTCAAAACAGTGYGAATATTACGGGACGAAGGGCAGTAAGtagttt ttaatatatttttatttatttatttatggtaRAAAATCaa[C]taatttWtatttttgag tGTGAACCGTTTCCTAATTAGAATAAAAAACTCTTGGGAAAATATTTCCATAAATACGAG Attactaaaaattaaattaacat |
| SEQ ID No. 32 | 1177586 | gGCAAACGTGTMCAGTCAAAACAGTGYGAATATTACGGGACGAAGGGCAGTAAGtagttt ttaatatatttttatttatttatttatggtaRAAAATCaa[A]taatttWtatttttgag tGTGAACCGTTTCCTAATTAGAATAAAAAACTCTTGGGAAAATATTTCCATAAATACGAG Attactaaaaattaaattaacat |
| SEQ ID No. 33 | 1206382 | TTAGTACAGTCGTCAATTAAAAATACTCCCGTTATACACGtgaataaaattttgttttca ctCRTTCGAGTGGTTAGtgagaatttattttWaaaaaaaa[T]tctagttTCTACCAAAA CTAAATTCTTTCCATtataactacggagtaatttgtatagcgattYccattttttttaagG AGATCTAATAGGAGACYTACTCA |
| SEQ ID No. 34 | 1206382 | TTAGTACAGTCGTCAATTAAAAATACTCCCGTTATACACGtgaataaaattttgttttca ctCRTTCGAGTGGTTAGtgagaatttattttWaaaaaaaa[A]tctagttTCTACCAAAA CTAAATTCTTTCCATtataactacggagtaatttgtatagcgattYccattttttttaagG AGATCTAATAGGAGACYTACTCA |
| SEQ ID No. 35 | 1216394 | TYTTTTYGTTGGGGTTGGWTTTCATGTATATGTTGCTGATTAAATACSagactgatgatg atKatgtgttTATGGGTTTTAAATCAGATTAAATATATGG[G]AAATGTAAGTTARTTGG GGATGCACataaggtgtttgMtgaaatgtctATKAgaaatgttgtttcttggacttAGAA TGATATACACTGTCGTCCWTTGG |
| SEQ ID No. 36 | 1216394 | TYTTTTYGTTGGGGTTGGWTTTCATGTATATGTTGCTGATTAAATACSagactgatgatg atKatgtgttTATGGGTTTTAAATCAGATTAAATATATGG[A]AAATGTAAGTTARTTGG GGATGCACataaggtgtttgMtgaaatgtctATKAgaaatgttgtttcttggacttAGAA TGATATACACTGTCGTCCWTTGG |

-continued

| SEQ ID No. | Genetic position* on Chr 4 (bp) | Sequence- SNP nucleotide is highlighted bold and in brackets |
|---|---|---|
| SEQ ID No. 37 | 1227120 | gATGGGARCACTATACATTGAGGTCGACTCAARTAACATATGATGCACGCATAACACCAA GAGTCSAAGACTCTGTTTTCTTGTataaagagagaagaaa[A]gaacacaGGTAACTGCA ACAATCACTTCATATGCACAACACARAGTTTAAGATAAACTAAATTTTAGATTTAGGCAA TCTGGAAAATTTATTACTTCATT |
| SEQ ID No. 38 | 1227120 | gATGGGARCACTATACATTGAGGTCGACTCAARTAACATATGATGCACGCATAACACCAA GAGTCSAAGACTCTGTTTTCTTGTataaagagagaagaaa[C]gaacacaGGTAACTGCA ACAATCACTTCATATGCACAACACARAGTTTAAGATAAACTAAATTTTAGATTTAGGCAA TCTGGAAAATTTATTACTTCATT |
| SEQ ID No. 39 | 1231945 | tatgCTRACCACAATGCTGTAAAATATTGGGCCCCATGTGCTTAWATAGGGAAATTTYCA TTGAGaagattRaaaattataacGAAGCCAAATGTTGTGA[T]CCCWCAGTAGTGTGTAC CCTKGCTTTTGTATRCTAACAGTTACACATCAATAATACAGAATRCCTCTAGACTCCAAG CAATGACATTCTGCAAGAGTACC |
| SEQ ID No. 40 | 1231945 | tatgCTRACCACAATGCTGTAAAATATTGGGCCCCATGTGCTTAWATAGGGAAATTTYCA TTGAGaagattRaaaattataacGAAGCCAAATGTTGTGA[C]CCCWCAGTAGTGTGTAC CCTKGCTTTTGTATRCTAACAGTTACACATCAATAATACAGAATRCCTCTAGACTCCAAG CAATGACATTCTGCAAGAGTACC |
| SEQ ID No. 41 | 1253108 | TGAGGGAGATAYGGGATTAATTCATATTGTCTTGGTGGAGAAGACGGCCGGCATAGATGG GAActtgagagggagagagagaaagattgagttaaaaaaa[A]tcagtaacaACATTGAA YGTTTTTCTTAAGctttttgtgaaaataaaataaacaaMtaaaTATTGAAGGATCTCATT TTTTAGCTCCGGTGAGTTAAACC |
| SEQ ID No. 42 | 1253108 | TGAGGGAGATAYGGGATTAATTCATATTGTCTTGGTGGAGAAGACGGCCGGCATAGATGG GAActtgagagggagagagagaaagattgagttaaaaaaa[G]tcagtaacaACATTGAA YGTTTTTCTTAAGctttttgtgaaaataaaataaacaaMtaaaTATTGAAGGATCTCATT TTTTAGCTCCGGTGAGTTAAACC |
| SEQ ID No. 43 | 1271037 | CGGTTGACCACACATTTGAGAAGCACTAATTASTCATAATGACAAACATATACGRAACCG ACCATGCATGTTTCTTGTCTCWATATTTATGCTTAATTAA[G]TCTTAACACAAAGGTTA ATTAAGGGGATGTGAAACTAATCACGTTCGATATAAGGTAATAGGGAGAATCATWGGYTT AAAATTAGTCATATAGCTACGCA |
| SEQ ID No. 44 | 1271037 | CGGTTGACCACACATTTGAGAAGCACTAATTASTCATAATGACAAACATATACGRAACCG ACCATGCATGTTTCTTGTCTCWATATTTATGCTTAATTAA[T]TCTTAACACAAAGGTTA ATTAAGGGGATGTGAAACTAATCACGTTCGATATAAGGTAATAGGGAGAATCATWGGYTT AAAATTAGTCATATAGCTACGCA |

*The reference genome is Xu, C., et al., Draft genome of spinach and transcriptome diversity of 120 Spinacia accessions, Nature Communications 2017.
Odd sequences = linked to resistance, Even sequences = alternative allele.

---

The invention claimed is:

1. A spinach plant resistant to *Peronospora farinosa* and *Stemphylium vesicarium*, comprising a genomic fragment of *Spinacia tetrandra* located on chromosome 4 of said spinach plant and between positions 8255074 and 8620598 of a spinach reference genome, said genomic fragment of *Spinacia tetrandra* lacking a lethal factor and providing *Peronospora farinosa* resistance;

comprising a genomic fragment located on chromosome 3 and between positions 1177586 and 1271037 of the spinach reference genome providing *Stemphylium vesicarium* resistance; and comprising a genomic fragment located on chromosome 3 and between positions 1201575 and 1220905 of the spinach reference genome providing Cucumber Mosaic Virus (CMV) resistance, wherein said genomic fragment of *Spinacia tetrandra* providing *Peronospora farinosa* resistance, said genomic fragment providing *Stemphylium vesicarium* resistance, and said genomic fragment providing Cucumber Mosaic Virus (CMV) resistance are obtained from a spinach plant deposited under deposit number NCIMB 43676.

2. The spinach plant according to claim 1 comprising in its genome one or more nucleotide sequences selected from the group consisting of SEQ ID Nos. 1, 3, 5, 7, 9, 11, 13, 15, 17, 19 and 21.

3. The spinach plant according to claim 1, comprising in its genome one or more nucleotide sequences selected from the group consisting of SEQ ID Nos. 31, 33, 35, 37, 39, 41, and 43.

4. The spinach plant according to claim 1, comprising in its genome SEQ ID Nos. 1, 3, 5, 7, 9, 11, 13, 15, 17, 19, 21, 31, 33, 35, 37, 39, 41, and 43.

5. The spinach plant according claim 1, comprising in its genome one or more nucleotide sequences selected from the group consisting of SEQ ID Nos. 23, 25, 27, and 29.

6. The spinach plant according to claim 1, comprising in its genome SEQ ID Nos. 1, 3, 5, 7, 9, 11, 13, 15, 17, 19, 21, 23, 25, 27, 29, 31, 33, 35, 37, 39, 41, and 43.

7. The spinach plant according to claim 1, wherein said *Peronospora farinosa* resistance comprises resistance to at least *Peronospora farinosa* isolates 1 to 17, UA2020-01E, and SP1924.

8. A plant cell, plant tissue, plant part or seed of a spinach plant according to claim 1; wherein the plant cell, plant tissue, plant part or seed each comprises: said genomic fragment of *Spinacia tetrandra* providing *Peronospora farinose* resistance, said genomic fragment providing *Stem-*

*phylium vesicarium* resistance, and said genomic fragment providing Cucumber Mosaic Virus (CMV) resistance obtained from a spinach plant deposited under deposit number NCIMB 43676.

9. A method of providing a spinach plant resistant to *Peronospora farinosa* and/or *Stemphylium vesicarium*, comprising crossing a spinach plant that is susceptible to *Peronospora farinosa* and/or *Stemphylium vesicarium* with the spinach plant according to claim 1 and selecting offspring that are resistant to *Peronospora farinosa* and/or *Stemphylium vesicarium*.

\* \* \* \* \*

SEQUENCE LISTING

<160> NUMBER OF SEQ ID NOS: 44

<210> SEQ ID NO 1
<211> LENGTH: 201
<212> TYPE: DNA
<213> ORGANISM: Spinacia tetrandra

<400> SEQUENCE: 1
tctggggttt tctgtaaatt gaaaaattgc aggaggttcc taaagcattg ctcccagttg       60
ggaatcggcc attagtgtcg tatgtattgg accttttgga gcaaagcaat ctcaaggata      120
ttattgtggt tcgtttcttt gcttttgatt gtttttttawt tgggaaaatg gcgaaattgk      180
gttgcaatat acttgtattt g                                                201

<210> SEQ ID NO 2
<211> LENGTH: 201
<212> TYPE: DNA
<213> ORGANISM: Brassica oleracea

<400> SEQUENCE: 2
tctggggttt tctgtaaatt gaaaaattgc aggaggttcc taaagcattg ctcccagttg       60

-continued

```
ggaatcggcc attagtgtcg tatgtattgg acctttttgga acaaagcaat ctcaaggata      120
ttattgtggt tcgtttcttt gcttttgatt gttttttawt tgggaaaatg gcgaaattgk      180
gttgcaatat acttgtattt g                                                 201

<210> SEQ ID NO 3
<211> LENGTH: 201
<212> TYPE: DNA
<213> ORGANISM: Spinacia tetrandra

<400> SEQUENCE: 3 gacctttttca actttaagaa gagattggac cttatcagct ttaagaatct gttattgtga       60
cttgaatcta gcgaagaaga ggaaagactg aaattcargc caagtgaagt gccccagaag      120
gacacgtaat aagatcctag gtgggatgac aaaggtgcaa agtccctcgt ctatcataag      180
gcaccctggg ctggctataa t                                                 201

<210> SEQ ID NO 4
<211> LENGTH: 201
<212> TYPE: DNA
<213> ORGANISM: Brassica oleracea

<400> SEQUENCE: 4 gacctttttca actttaagaa gagattggac cttatcagct ttaagaatct gttattgtga       60
cttgaatcta gcgaagaaga ggaaagactg aaattcargc taagtgaagt gccccagaag      120
gacacgtaat aagatcctag gtgggatgac aaaggtgcaa agtccctcgt ctatcataag      180
gcaccctggg ctggctataa t                                                 201

<210> SEQ ID NO 5
<211> LENGTH: 201
<212> TYPE: DNA
<213> ORGANISM: Spinacia tetrandra

<400> SEQUENCE: 5
tcattctgat cataatcatc tgagaataaa catttcacca aatacatgag acaattcaat       60
caaatactgc catattatgc ttattagtta ttagcccgca catcctttaa aggcaatata      120
tactacacct ttcacaaatg aatgagccac aaacaataat ttctcaatca agcaataagt      180
taatttacac atgcwataac t                                                 201

<210> SEQ ID NO 6
<211> LENGTH: 201
<212> TYPE: DNA
<213> ORGANISM: Brassica oleracea

<400> SEQUENCE: 6
tcattctgat cataatcatc tgagaataaa catttcacca aatacatgag acaattcaat       60
caaatactgc catattatgc ttattagtta ttagcccgca catcctttaa aggcaatata      120
tactacacct ttcacaaatg aatgagccac aaacaataat ttctcaatca agcaataagt      180
taatttacac atgcwataac t                                                 201

<210> SEQ ID NO 7
<211> LENGTH: 201
<212> TYPE: DNA
<213> ORGANISM: Spinacia tetrandra

<400> SEQUENCE: 7
atmaatccat ctgctcattt atcgatttca gataaacatc tttyaccagg ttcgtgattc       60
```

-continued

```
ttctctttct ctctcttcga tttttcttca gaattagtta tyttttcttt aattatttgg      120
tcgcgattgg tattttatgc cctaattacg tgattgaatt gcgttttgag cktcaatttk      180
ggatgtattg tttgtagaaa g                                                201

<210> SEQ ID NO 8
<211> LENGTH: 201
<212> TYPE: DNA
<213> ORGANISM: Brassica oleracea

<400> SEQUENCE: 8
atmaatccat ctgctcattt atcgatttca gataaacatc tttyaccagg ttcgtgattc       60
ttctctttct ctctcttcga tttttcttca gaattagtta ayttttcttt aattatttgg      120
tcgcgattgg tattttatgc cctaattacg tgattgaatt gcgttttgag cktcaatttk      180
ggatgtattg tttgtagaaa g                                                201

<210> SEQ ID NO 9
<211> LENGTH: 201
<212> TYPE: DNA
<213> ORGANISM: Spinacia tetrandra

<400> SEQUENCE: 9
gagtttgatt cttccagttt cggacasaga ggaaaatttc tcaaattatc acaaaatgta       60
attaacagat gagaaaggtg atggaacgaa taygaatgtg tttgaaaccc tgctacttct      120
cgtgtctcac ccatatctga ttctratttc caccatcctt ccaactttgg catactccaa      180
agctcaagct tttcaaggga t                                                201

<210> SEQ ID NO 10
<211> LENGTH: 201
<212> TYPE: DNA
<213> ORGANISM: Brassica oleracea

<400> SEQUENCE: 10
gagtttgatt cttccagttt cggacasaga ggaaaatttc tcaaattatc acaaaatgta       60
attaacagat gagaaaggtg atggaacgaa taygaatgtg attgaaaccc tgctacttct      120
cgtgtctcac ccatatctga ttctratttc caccatcctt ccaactttgg catactccaa      180
agctcaagct tttcaaggga t                                                201

<210> SEQ ID NO 11
<211> LENGTH: 201
<212> TYPE: DNA
<213> ORGANISM: Spinacia tetrandra

<400> SEQUENCE: 11
aagctcaagc ttttcaaggg atggaaagaa aaccaagtca acatctgctc ctccatgatt       60
tgaccctcct gatgttgatg caaccccttc tgcgctgata atactattct ccatayacac      120
cacttcaytc aaatatcgta atgtaaggaa tttcaaatga cgcagttgac tcatcaatgg      180
aagatgctcc aaccttgtac a                                                201

<210> SEQ ID NO 12
<211> LENGTH: 201
<212> TYPE: DNA
<213> ORGANISM: Brassica oleracea

<400> SEQUENCE: 12
```

-continued

```
aagctcaagc ttttcaaggg atggaaagaa aaccaagtca acatctgctc ctccatgatt        60
tgaccctcct gatgttgatg caacccttc tgcgctgata gtactattct ccatayacac       120
cacttcaytc aaatatcgta atgtaaggaa tttcaaatga cgcagttgac tcatcaatgg       180
aagatgctcc aaccttgtac a                                                201
```

```
<210> SEQ ID NO 13
<211> LENGTH: 201
<212> TYPE: DNA
<213> ORGANISM: Spinacia tetrandra

<400> SEQUENCE: 13 tttttttkaca taaattacca tatagtggct atgattgctg aaatttttca aatctcccag        60
ctcaccaaca ccgtttgacc cccgattcca gctatttctt tttctgctca ctacaaaccc       120
tgtcagtyta tgcagagatg tcatgctatt catcccccgr ggcatatgyg acaaactctt       180
acagccttgt atatctaggt g                                                201
```

```
<210> SEQ ID NO 14
<211> LENGTH: 201
<212> TYPE: DNA
<213> ORGANISM: Brassica oleracea

<400> SEQUENCE: 14 tttttttkaca taaattacca tatagtggct atgattgctg aaatttttca aatctcccag        60
ctcaccaaca ccgtttgacc cccgattcca gctatttctt gttctgctca ctacaaaccc       120
tgtcagtyta tgcagagatg tcatgctatt catcccccgr ggcatatgyg acaaactctt       180
acagccttgt atatctaggt g                                                201
```

```
<210> SEQ ID NO 15
<211> LENGTH: 201
<212> TYPE: DNA
<213> ORGANISM: Spinacia tetrandra

<400> SEQUENCE: 15
cctttcaagt aatacagagt taggtccaag tttaggatca ggtcaagcaa aacaactgta        60
taaccatact caacacagcc ccaccggagt caagtcgaaa taaccaagtc tttgaaagag       120
aagacatgac cttatgttcg grcccaacgc acaaaatcaa tagagtagaa atgtacaatt       180
catttccatt gctatgtakt g                                                201
```

```
<210> SEQ ID NO 16
<211> LENGTH: 201
<212> TYPE: DNA
<213> ORGANISM: Brassica oleracea

<400> SEQUENCE: 16
cctttcaagt aatacagagt taggtccaag tttaggatca ggtcaagcaa aacaactgta        60
taaccatact caacacagcc ccaccggagt caagtcgaaa caaccaagtc tttgaaagag       120
aagacatgac cttatgttcg grcccaacgc acaaaatcaa tagagtagaa atgtacaatt       180
catttccatt gctatgtakt g                                                201
```

```
<210> SEQ ID NO 17
<211> LENGTH: 201
<212> TYPE: DNA
<213> ORGANISM: Spinacia tetrandra

<400> SEQUENCE: 17
```

-continued

```
ataggttgtt tagaacttta tcaattacta ctaactactc cgtactcttc actgataagt        60
tgtcaattac taactaatta ctacataggt tttgttaaaa gttgtcaatt attagctatt       120
tttctaacaa wggaggtcaa ttactaattc gttgtcaatt aatacgtttt ccgcccaatt       180
agtcgactaa tcacatcata a                                                 201
```

```
<210> SEQ ID NO 18
<211> LENGTH: 201
<212> TYPE: DNA
<213> ORGANISM: Brassica oleracea

<400> SEQUENCE: 18
ataggttgtt tagaacttta tcaattacta ctaactactc cgtactcttc actgataagt        60
tgtcaattac taactaatta ctacataggt tttgttaaaa attgtcaatt attagctatt       120
tttctaacaa wggaggtcaa ttactaattc gttgtcaatt aatacgtttt ccgcccaatt       180
agtcgactaa tcacatcata a                                                 201
```

```
<210> SEQ ID NO 19
<211> LENGTH: 201
<212> TYPE: DNA
<213> ORGANISM: Spinacia tetrandra

<400> SEQUENCE: 19 agatattta accgataatt cgatattatc cagcttgtac taataataaa taataaatta        60
tataatcaaa tacaaaaaat atttacaatt ttaaaatcaa ttttcagtgt tatattgtta       120
tccaaascca ataaggataa gttaattatc ttataaacgt gcaattaata catacaatcc       180
ttgtaaattc agttttactt c                                                 201
```

```
<210> SEQ ID NO 20
<211> LENGTH: 201
<212> TYPE: DNA
<213> ORGANISM: Brassica oleracea

<400> SEQUENCE: 20 agatattta accgataatt cgatattatc cagcttgtac taataataaa taataaatta        60
tataatcaaa tacaaaaaat atttacaatt ttaaaatcaa atttcagtgt tatattgtta       120
tccaaascca ataaggataa gttaattatc ttataaacgt gcaattaata catacaatcc       180
ttgtaaattc agttttactt c                                                 201
```

```
<210> SEQ ID NO 21
<211> LENGTH: 201
<212> TYPE: DNA
<213> ORGANISM: Spinacia tetrandra

<400> SEQUENCE: 21
tttctttact tatatatttc tctttttttca ccctttttact tctcactacc cacataataa        60
camtctccca cagtcccacc ctttcccct ccatawccca gcaaaattac aagttcattt       120
ctcgtctttc gggtgagatt ctcactgcaa agtgaccaca ttactcttcc aaccacaaaa       180
ttaattaatc aaattactac a                                                 201
```

```
<210> SEQ ID NO 22
<211> LENGTH: 201
<212> TYPE: DNA
<213> ORGANISM: Brassica oleracea
```

<400> SEQUENCE: 22
tttctttact tatatatttc tcttttttca ccctttttact tctcactacc cacataataa          60
camtctccca cagtcccacc ctttcccct ccatawccca tcaaaattac aagttcattt          120
ctcgtctttc gggtgagatt ctcactgcaa agtgaccaca ttactcttcc aaccacaaaa          180
ttaattaatc aaattactac a          201

<210> SEQ ID NO 23
<211> LENGTH: 201
<212> TYPE: DNA
<213> ORGANISM: Brassica oleracea

<400> SEQUENCE: 23
ccctccgtat ttttcttaa tgttataatt gcactatttg atgtttcacg tttgtcaatg          60
cgaaacttta gcacaattrg ttagtaagac atcacatgtc tgatrtcttt atccatttga          120
atgggccata tgttggccat atacatttct aaaaaggtat gggctacaac gcctacaagt          180
aacaactatc ataattataa g          201

<210> SEQ ID NO 24
<211> LENGTH: 201
<212> TYPE: DNA
<213> ORGANISM: Brassica oleracea

<400> SEQUENCE: 24
ccctccgtat ttttcttaa tgttataatt gcactatttg atgtttcacg tttgtcaatg          60
cgaaacttta gcacaattrg ttagtaagac atcacatgtc agatrtcttt atccatttga          120
atgggccata tgttggccat atacatttct aaaaaggtat gggctacaac gcctacaagt          180
aacaactatc ataattataa g          201

<210> SEQ ID NO 25
<211> LENGTH: 201
<212> TYPE: DNA
<213> ORGANISM: Brassica oleracea

<400> SEQUENCE: 25
atggraaatg taagttartt ggggatgcac ataaggtgtt tgmtgaaatg tctatkagaa          60
atgttgtttc ttggacttag aatgatatac actgtcgtcc attggtttcc aatcttacat          120
ttggtttktg ttttcttagt ttgtttcttt aatcaacacc arcccatttt ttttaaacta          180
cctgcaacta ytaawtttca t          201

<210> SEQ ID NO 26
<211> LENGTH: 201
<212> TYPE: DNA
<213> ORGANISM: Brassica oleracea

<400> SEQUENCE: 26
atggraaatg taagttartt ggggatgcac ataaggtgtt tgmtgaaatg tctatkagaa          60
atgttgtttc ttggacttag aatgatatac actgtcgtcc tttggtttcc aatcttacat          120
ttggtttktg ttttcttagt ttgtttcttt aatcaacacc arcccatttt ttttaaacta          180
cctgcaacta ytaawtttca t          201

<210> SEQ ID NO 27
<211> LENGTH: 201
<212> TYPE: DNA
<213> ORGANISM: Brassica oleracea -continued

```
<400> SEQUENCE: 27
caaacttgga aaataatgac agaaaaatgc taagttaata taggaaacta catcattttc      60
actcgaaaag attagaggaa ttcatwttcg tcttcctccc attgayttca tgtgccgtaa     120
atcttytgac tgtctatatt ggtacaagtr atttcaggta tatacattgg ttaatccatt    180
ttaatctgta tctgccggtg t                                              201

<210> SEQ ID NO 28
<211> LENGTH: 201
<212> TYPE: DNA
<213> ORGANISM: Brassica oleracea

<400> SEQUENCE: 28
caaacttgga aaataatgac agaaaaatgc taagttaata taggaaacta catcattttc      60
actcgaaaag attagaggaa ttcatwttcg tcttcctccc cttgayttca tgtgccgtaa     120
atcttytgac tgtctatatt ggtacaagtr atttcaggta tatacattgg ttaatccatt    180
ttaatctgta tctgccggtg t                                              201

<210> SEQ ID NO 29
<211> LENGTH: 201
<212> TYPE: DNA
<213> ORGANISM: Brassica oleracea

<400> SEQUENCE: 29
tattatgamg ggtcaacaat tatgtaatat atagggaagt agaaagtctg ggatgttacc      60
tgaagagtct ccttgcctgc aaagttttaa gctgcaagaa ggtatttgrc aataattaat     120
racattkcac aacaaagatt atgcacattt ttctttaaaa atcaagagaa acttgtagat    180
gtaccgtaaa taggaacatc t                                              201

<210> SEQ ID NO 30
<211> LENGTH: 201
<212> TYPE: DNA
<213> ORGANISM: Brassica oleracea

<400> SEQUENCE: 30
tattatgamg ggtcaacaat tatgtaatat atagggaagt agaaagtctg ggatgttacc      60
tgaagagtct ccttgcctgc aaagttttaa gctgcaagaa agtatttgrc aataattaat     120
racattkcac aacaaagatt atgcacattt ttctttaaaa atcaagagaa acttgtagat    180
gtaccgtaaa taggaacatc t                                              201

<210> SEQ ID NO 31
<211> LENGTH: 201
<212> TYPE: DNA
<213> ORGANISM: Brassica oleracea

<400> SEQUENCE: 31
ggcaaacgtg tmcagtcaaa acagtgygaa tattacggga cgaagggcag taagtagttt      60
ttaatatatt tttatttatt tatttatggt araaaatcaa ctaatttwta tttttgagtg     120
tgaaccgttt cctaattaga ataaaaaact cttgggaaaa tatttccata aatacgagat    180
tactaaaaat taaattaaca t                                              201

<210> SEQ ID NO 32
<211> LENGTH: 201
<212> TYPE: DNA
```

<213> ORGANISM: Brassica oleracea

<400> SEQUENCE: 32

```
ggcaaacgtg tmcagtcaaa acagtgygaa tattacggga cgaagggcag taagtagttt      60
ttaatatatt tttatttatt tatttatggt araaaatcaa ataatttwta tttttgagtg     120
tgaaccgttt cctaattaga ataaaaaact cttgggaaaa tatttccata aatacgagat     180
tactaaaaat taaattaaca t                                                201
```

<210> SEQ ID NO 33
<211> LENGTH: 201
<212> TYPE: DNA
<213> ORGANISM: Brassica oleracea

<400> SEQUENCE: 33

```
ttagtacagt cgtcaattaa aaatactccc gttatacacg tgaataaaat tttgtttttca      60 ctcrttcgag tggttagtga gaatttattt twaaaaaaaa ttctagtttc taccaaaact     120
aaattctttc cattataact acggagtaat ttgtatagcg attyccattt ttttaaggag     180
atctaatagg agacytactc a                                                201
```

<210> SEQ ID NO 34
<211> LENGTH: 201
<212> TYPE: DNA
<213> ORGANISM: Brassica oleracea

<400> SEQUENCE: 34

```
ttagtacagt cgtcaattaa aaatactccc gttatacacg tgaataaaat tttgtttttca      60 ctcrttcgag tggttagtga gaatttattt twaaaaaaaa atctagtttc taccaaaact     120
aaattctttc cattataact acggagtaat ttgtatagcg attyccattt ttttaaggag     180
atctaatagg agacytactc a                                                201
```

<210> SEQ ID NO 35
<211> LENGTH: 201
<212> TYPE: DNA
<213> ORGANISM: Brassica oleracea

<400> SEQUENCE: 35

```
tyttttygtt ggggttggwt ttcatgtata tgttgctgat taaatacsag actgatgatg      60
atkatgtgtt tatgggtttt aaatcagatt aaatatatgg gaaatgtaag ttarttgggg     120
atgcacataa ggtgtttgmt gaaatgtcta tkagaaatgt tgtttcttgg acttagaatg     180
atatacactg tcgtccwttg g                                                201
```

<210> SEQ ID NO 36
<211> LENGTH: 201
<212> TYPE: DNA
<213> ORGANISM: Brassica oleracea

<400> SEQUENCE: 36

```
tyttttygtt ggggttggwt ttcatgtata tgttgctgat taaatacsag actgatgatg      60
atkatgtgtt tatgggtttt aaatcagatt aaatatatgg aaaatgtaag ttarttgggg     120
atgcacataa ggtgtttgmt gaaatgtcta tkagaaatgt tgtttcttgg acttagaatg     180
atatacactg tcgtccwttg g                                                201
```

<210> SEQ ID NO 37
<211> LENGTH: 201

```
<212> TYPE: DNA
<213> ORGANISM: Brassica oleracea

<400> SEQUENCE: 37
gatgggarca ctatacattg aggtcgactc aartaacata tgatgcacgc ataacaccaa        60
gagtcsaaga ctctgttttc ttgtataaag agagaagaaa agaacacagg taactgcaac       120
aatcacttca tatgcacaac acaragttta agataaacta aattttagat ttaggcaatc       180
tggaaaattt attacttcat t                                                 201

<210> SEQ ID NO 38
<211> LENGTH: 201
<212> TYPE: DNA
<213> ORGANISM: Brassica oleracea

<400> SEQUENCE: 38
gatgggarca ctatacattg aggtcgactc aartaacata tgatgcacgc ataacaccaa        60
gagtcsaaga ctctgttttc ttgtataaag agagaagaaa cgaacacagg taactgcaac       120
aatcacttca tatgcacaac acaragttta agataaacta aattttagat ttaggcaatc       180
tggaaaattt attacttcat t                                                 201

<210> SEQ ID NO 39
<211> LENGTH: 201
<212> TYPE: DNA
<213> ORGANISM: Brassica oleracea

<400> SEQUENCE: 39
tatgctracc acaatgctgt aaaatattgg gccccatgtg cttawatagg gaaatttyca        60
ttgagaagat traaaattat aacgaagcca aatgttgtga tcccwcagta gtgtgtaccc       120
tkgcttttgt atrctaacag ttacacatca ataatacaga atrcctctag actccaagca       180
atgacattct gcaagagtac c                                                 201

<210> SEQ ID NO 40
<211> LENGTH: 201
<212> TYPE: DNA
<213> ORGANISM: Brassica oleracea

<400> SEQUENCE: 40
tatgctracc acaatgctgt aaaatattgg gccccatgtg cttawatagg gaaatttyca        60
ttgagaagat traaaattat aacgaagcca aatgttgtga ccccwcagta gtgtgtaccc       120
tkgcttttgt atrctaacag ttacacatca ataatacaga atrcctctag actccaagca       180
atgacattct gcaagagtac c                                                 201

<210> SEQ ID NO 41
<211> LENGTH: 201
<212> TYPE: DNA
<213> ORGANISM: Brassica oleracea

<400> SEQUENCE: 41
tgagggagat aygggattaa ttcatattgt cttggtggag aagacggccg gcatagatgg        60
gaacttgaga gggagagaga gaaagattga gttaaaaaaa atcagtaaca acattgaayg       120
tttttcttaa gcttttgtg aaaataaaat aaacaamtaa atattgaagg atctcatttt       180
ttagctccgg tgagttaaac c                                                 201

<210> SEQ ID NO 42
```

-continued

```
<211> LENGTH: 201
<212> TYPE: DNA
<213> ORGANISM: Brassica oleracea

<400> SEQUENCE: 42
tgagggagat aygggattaa ttcatattgt cttggtggag aagacggccg gcatagatgg      60
gaacttgaga gggagagaga gaaagattga gttaaaaaaa gtcagtaaca acattgaayg     120
tttttcttaa gcttttgtg aaaataaaat aaacaamtaa atattgaagg atctcatttt     180
ttagctccgg tgagttaaac c                                              201

<210> SEQ ID NO 43
<211> LENGTH: 201
<212> TYPE: DNA
<213> ORGANISM: Brassica oleracea

<400> SEQUENCE: 43
cggttgacca cacatttgag aagcactaat tastcataat gacaaacata tacgraaccg      60
accatgcatg tttcttgtct cwatatttat gcttaattaa gtcttaacac aaaggttaat     120
taaggggatg tgaaactaat cacgttcgat ataaggtaat agggagaatc atwggyttaa     180
aattagtcat atagctacgc a                                              201

<210> SEQ ID NO 44
<211> LENGTH: 201
<212> TYPE: DNA
<213> ORGANISM: Brassica oleracea

<400> SEQUENCE: 44
cggttgacca cacatttgag aagcactaat tastcataat gacaaacata tacgraaccg      60
accatgcatg tttcttgtct cwatatttat gcttaattaa ttcttaacac aaaggttaat     120
taaggggatg tgaaactaat cacgttcgat ataaggtaat agggagaatc atwggyttaa     180
aattagtcat atagctacgc a                                              201
```